(12) United States Patent
Grace

(10) Patent No.: US 9,402,619 B2
(45) Date of Patent: Aug. 2, 2016

(54) RIGIDLY-LINKED ARTICULATING WRIST WITH DECOUPLED MOTION TRANSMISSION

(71) Applicant: Intuitive Surgical Operations, Inc., Sunnyvale, CA (US)

(72) Inventor: Kenneth Grace, Knoxville, TN (US)

(73) Assignee: Intuitive Surgical Operation, Inc., Sunnyvale, CA (US)

(*) Notice: Subject to any disclaimer, the term of this patent is extended or adjusted under 35 U.S.C. 154(b) by 0 days.

(21) Appl. No.: 14/499,373

(22) Filed: Sep. 29, 2014

(65) Prior Publication Data

US 2015/0018846 A1    Jan. 15, 2015

Related U.S. Application Data

(60) Continuation of application No. 13/633,963, filed on Oct. 3, 2012, now Pat. No. 8,845,681, which is a continuation of application No. 11/948,052, filed on Nov. 30, 2007, now Pat. No. 8,292,916, which is a division of application No. 10/013,170, filed on Jun. 7, 2002, now Pat. No. Re. 43,049, which is a continuation-in-part of application No. 09/262,134, filed on Mar. 3, 1999, now Pat. No. 6,436,107, which is a continuation-in-part of application No. 08/873,190, filed on Jun. 11, 1997, now Pat. No. 6,102,850, which is a continuation-in-part of application No. 08/755,063, filed on Nov. 22, 1996, now Pat. No. 5,855,583.

(51) Int. Cl.
*A61B 17/00* (2006.01)
*A61B 17/04* (2006.01)
*A61B 17/062* (2006.01)
*A61B 17/29* (2006.01)

(52) U.S. Cl.
CPC ........... *A61B 17/0469* (2013.01); *A61B 17/062* (2013.01); *A61B 34/75* (2016.02); *A61B 2017/2927* (2013.01); *A61B 2017/2936* (2013.01); *Y10T 74/20317* (2015.01)

(58) Field of Classification Search
CPC .... A61B 17/04; A61B 17/00; A61B 17/0469; A61B 2017/2936
USPC ........................ 606/1, 130, 205, 208; 600/102
See application file for complete search history.

(56) References Cited

U.S. PATENT DOCUMENTS 977,825 A    12/1910   George
1,327,577 A   1/1920   Turner
(Continued)

FOREIGN PATENT DOCUMENTS

DE    9204118 U1    5/1992
DE    4101242 A1    7/1992
(Continued)

OTHER PUBLICATIONS

Abstract of a presentation "3-D Vision Technology Applied to Advanced Minimally Invasive Surgery Systems," (Session 15/3) given at the 3rd World Congress of Endoscopic Surgery in Bordeaux, Jun. 18-20, 1992, 1 page.

(Continued)

*Primary Examiner* — Victor Nguyen

(57) ABSTRACT

The present invention is a device having a rigidly linked jaw that is decoupled from an articulating wrist. The device provides for articulating motion as well as actuation that may be used in grasping, cutting, suturing or the like.

4 Claims, 3 Drawing Sheets

(56) References Cited

U.S. PATENT DOCUMENTS

| | | |
|---|---|---|
| 3,171,549 A | 3/1965 | Orloff |
| 3,280,991 A | 10/1966 | Melton et al. |
| 3,628,535 A | 12/1971 | Ostrowsky et al. |
| 3,698,791 A | 10/1972 | Walchle et al. |
| 3,710,798 A | 1/1973 | Bredemeier |
| 3,961,921 A | 6/1976 | Heiman et al. |
| 4,041,942 A | 8/1977 | Dougan et al. |
| 4,058,001 A | 11/1977 | Waxman |
| 4,078,568 A | 3/1978 | Etes et al. |
| 4,128,880 A | 12/1978 | Cray, Jr. |
| 4,160,508 A | 7/1979 | Frosch et al. |
| 4,221,997 A | 9/1980 | Flemming |
| 4,367,998 A | 1/1983 | Causer |
| 4,375,674 A | 3/1983 | Thornton |
| 4,401,852 A | 8/1983 | Noso et al. |
| 4,456,761 A | 6/1984 | Krapcho |
| 4,456,961 A | 6/1984 | Price et al. |
| 4,460,302 A | 7/1984 | Moreau et al. |
| 4,474,174 A | 10/1984 | Petruzzi |
| 4,491,135 A | 1/1985 | Klein |
| 4,503,854 A | 3/1985 | Jako |
| 4,517,963 A | 5/1985 | Michel |
| 4,523,884 A | 6/1985 | Clement et al. |
| 4,586,398 A | 5/1986 | Yindra |
| 4,598,725 A | 7/1986 | Brewer |
| 4,604,016 A | 8/1986 | Joyce |
| 4,616,637 A | 10/1986 | Caspari et al. |
| 4,624,011 A | 11/1986 | Watanabe et al. |
| 4,633,389 A | 12/1986 | Tanaka et al. |
| 4,635,292 A | 1/1987 | Mori et al. |
| 4,635,479 A | 1/1987 | Salisbury, Jr. |
| 4,641,292 A | 2/1987 | Tunnell et al. |
| 4,650,388 A | 3/1987 | Frioux et al. |
| 4,655,257 A | 4/1987 | Iwashita |
| 4,672,963 A | 6/1987 | Barken |
| 4,676,243 A | 6/1987 | Clayman |
| 4,728,974 A | 3/1988 | Nio et al. |
| 4,750,636 A | 6/1988 | Wortham |
| 4,762,455 A | 8/1988 | Coughlan et al. |
| 4,791,934 A | 12/1988 | Brunnett |
| 4,791,940 A | 12/1988 | Hirschfeld et al. |
| 4,794,912 A | 1/1989 | Lia |
| 4,799,779 A | 1/1989 | Mesmer |
| 4,800,614 A | 1/1989 | Kopco et al. |
| 4,815,006 A | 3/1989 | Andersson et al. |
| 4,815,450 A | 3/1989 | Patel |
| 4,817,592 A | 4/1989 | Auchinleck et al. |
| 4,831,547 A | 5/1989 | Ishiguro et al. |
| 4,837,734 A | 6/1989 | Ichikawa et al. |
| 4,837,754 A | 6/1989 | Nakagawa |
| 4,839,838 A | 6/1989 | LaBiche et al. |
| 4,852,083 A | 7/1989 | Niehaus et al. |
| 4,853,874 A | 8/1989 | Iwamoto et al. |
| 4,854,301 A | 8/1989 | Nakajima |
| 4,860,215 A | 8/1989 | Seraji |
| 4,863,133 A | 9/1989 | Bonnell |
| 4,883,400 A | 11/1989 | Kuban et al. |
| 4,896,673 A | 1/1990 | Rose et al. |
| 4,930,494 A | 6/1990 | Takehana et al. |
| 4,945,479 A | 7/1990 | Rusterholz et al. |
| 4,949,717 A | 8/1990 | Shaw |
| 4,954,952 A | 9/1990 | Ubhayakar et al. |
| 4,965,417 A | 10/1990 | Massie |
| 4,969,709 A | 11/1990 | Sogawa et al. |
| 4,969,890 A | 11/1990 | Sugita et al. |
| 4,974,191 A | 11/1990 | Amirghodsi et al. |
| 4,979,933 A | 12/1990 | Runge |
| 4,979,949 A | 12/1990 | Matsen, III |
| 4,980,626 A | 12/1990 | Hess et al. |
| 4,989,253 A | 1/1991 | Liang et al. |
| 4,996,975 A | 3/1991 | Nakamura |
| 5,007,300 A | 4/1991 | Siva |
| 5,019,968 A | 5/1991 | Wang et al. |
| 5,020,001 A | 5/1991 | Yamamoto et al. |
| 5,024,652 A | 6/1991 | Dumenek et al. |
| 5,046,375 A | 9/1991 | Salisbury, Jr. |
| 5,053,687 A | 10/1991 | Merlet |
| 5,053,975 A | 10/1991 | Tsuchihashi et al. |
| 5,060,632 A | 10/1991 | Hibino et al. |
| 5,065,741 A | 11/1991 | Uchiyama et al. |
| 5,078,140 A | 1/1992 | Kwoh |
| 5,086,401 A | 2/1992 | Glassman et al. |
| 5,091,656 A | 2/1992 | Gahn |
| 5,097,829 A | 3/1992 | Quisenberry |
| 5,097,839 A | 3/1992 | Allen |
| 5,098,426 A | 3/1992 | Sklar et al. |
| 5,100,138 A | 3/1992 | Wilde |
| 5,105,367 A | 4/1992 | Tsuchihashi et al. |
| 5,107,080 A | 4/1992 | Rosen |
| 5,109,499 A | 4/1992 | Inagami et al. |
| 5,123,095 A | 6/1992 | Papadopoulos et al. |
| 5,131,105 A | 7/1992 | Harrawood et al. |
| 5,142,930 A | 9/1992 | Allen et al. |
| 5,145,227 A | 9/1992 | Monford, Jr. |
| 5,150,704 A | 9/1992 | Tatebayashi et al. |
| 5,166,513 A | 11/1992 | Keenan et al. |
| 5,175,694 A | 12/1992 | Amato |
| 5,182,641 A | 1/1993 | Diner et al. |
| 5,184,601 A | 2/1993 | Putman |
| 5,186,232 A | 2/1993 | Zahner |
| 5,187,574 A | 2/1993 | Kosemura et al. |
| 5,188,111 A | 2/1993 | Yates et al. |
| 5,196,688 A | 3/1993 | Hesse et al. |
| 5,198,894 A | 3/1993 | Hicks |
| 5,201,325 A | 4/1993 | McEwen et al. |
| 5,201,743 A | 4/1993 | Haber et al. |
| 5,213,141 A | 5/1993 | Dorman |
| 5,217,003 A | 6/1993 | Wilk |
| 5,217,478 A | 6/1993 | Rexroth |
| 5,221,283 A | 6/1993 | Chang |
| 5,228,429 A | 7/1993 | Hatano |
| 5,230,623 A | 7/1993 | Guthrie et al. |
| 5,236,432 A | 8/1993 | Matsen, III et al. |
| 5,239,883 A | 8/1993 | Rosheim |
| 5,239,981 A | 8/1993 | Anapliotis |
| 5,251,127 A | 10/1993 | Raab |
| 5,257,999 A | 11/1993 | Slanetz, Jr. |
| 5,271,384 A | 12/1993 | McEwen et al. |
| 5,274,500 A | 12/1993 | Dunn |
| 5,275,608 A | 1/1994 | Forman et al. |
| 5,279,309 A | 1/1994 | Taylor et al. |
| 5,282,806 A | 2/1994 | Haber et al. |
| 5,282,826 A | 2/1994 | Quadri |
| 5,289,273 A | 2/1994 | Lang |
| 5,289,365 A | 2/1994 | Caldwell et al. |
| 5,299,288 A | 3/1994 | Glassman et al. |
| 5,300,926 A | 4/1994 | Stoeckl |
| 5,301,657 A | 4/1994 | Lafferty et al. |
| 5,303,148 A | 4/1994 | Mattson et al. |
| 5,304,185 A | 4/1994 | Taylor |
| 5,305,203 A | 4/1994 | Raab |
| 5,305,427 A | 4/1994 | Nagata |
| 5,309,717 A | 5/1994 | Minch |
| 5,313,306 A | 5/1994 | Kuban et al. |
| 5,320,630 A | 6/1994 | Ahmed |
| 5,331,413 A | 7/1994 | Diner |
| 5,337,732 A | 8/1994 | Grundfest et al. |
| 5,339,799 A | 8/1994 | Kami et al. |
| 5,343,385 A | 8/1994 | Joskowicz et al. |
| 5,343,391 A | 8/1994 | Mushabac |
| 5,345,538 A | 9/1994 | Narayannan et al. |
| 5,350,355 A | 9/1994 | Sklar |
| 5,357,962 A | 10/1994 | Green |
| 5,368,015 A | 11/1994 | Wilk |
| 5,368,428 A | 11/1994 | Hussey et al. |
| 5,371,536 A | 12/1994 | Yamaguchi |
| 5,382,885 A | 1/1995 | Salcudean et al. |
| 5,388,987 A | 2/1995 | Badoz et al. |
| 5,395,369 A | 3/1995 | McBrayer et al. |
| 5,397,323 A | 3/1995 | Taylor et al. |
| 5,402,801 A | 4/1995 | Taylor |
| 5,403,319 A | 4/1995 | Matsen, III et al. |
| 5,408,409 A | 4/1995 | Glassman et al. |
| 5,410,638 A | 4/1995 | Colgate et al. |

(56) References Cited

U.S. PATENT DOCUMENTS

| | | | |
|---|---|---|---|
| 5,413,092 | A | 5/1995 | Williams, III et al. |
| 5,417,210 | A | 5/1995 | Funda et al. |
| 5,417,701 | A | 5/1995 | Holmes |
| 5,422,521 | A | 6/1995 | Neer et al. |
| 5,429,142 | A | 7/1995 | Szabo et al. |
| 5,431,645 | A | 7/1995 | Smith et al. |
| 5,434,457 | A | 7/1995 | Josephs et al. |
| 5,441,042 | A | 8/1995 | Putman |
| 5,442,728 | A | 8/1995 | Kaufman et al. |
| 5,443,484 | A | 8/1995 | Kirsch et al. |
| 5,445,166 | A | 8/1995 | Taylor |
| 5,451,852 | A | 9/1995 | Gusakov |
| 5,451,924 | A | 9/1995 | Massimino et al. |
| 5,454,827 | A | 10/1995 | Aust et al. |
| 5,455,766 | A | 10/1995 | Scheller et al. |
| 5,458,547 | A | 10/1995 | Teraoka et al. |
| 5,458,574 | A | 10/1995 | Machold et al. |
| 5,467,223 | A | 11/1995 | Cleveland, Jr. et al. |
| 5,474,571 | A | 12/1995 | Lang |
| 5,476,010 | A | 12/1995 | Fleming et al. |
| 5,478,351 | A | 12/1995 | Meade et al. |
| 5,483,961 | A | 1/1996 | Kelly et al. |
| 5,489,292 | A | 2/1996 | Tovey et al. |
| 5,490,117 | A | 2/1996 | Oda et al. |
| 5,490,843 | A | 2/1996 | Hildwein et al. |
| 5,506,912 | A | 4/1996 | Nagasaki et al. |
| 5,512,919 | A | 4/1996 | Araki |
| 5,515,478 | A | 5/1996 | Wang |
| 5,524,180 | A | 6/1996 | Wang et al. |
| 5,544,654 | A | 8/1996 | Murphy et al. |
| 5,553,198 | A | 9/1996 | Wang et al. |
| 5,562,503 | A | 10/1996 | Ellman et al. |
| 5,571,110 | A | 11/1996 | Matsen, III et al. |
| 5,572,999 | A | 11/1996 | Funda et al. |
| 5,599,151 | A | 2/1997 | Daum et al. |
| 5,609,560 | A | 3/1997 | Ichikawa et al. |
| 5,622,170 | A | 4/1997 | Schulz |
| 5,626,595 | A | 5/1997 | Sklar et al. |
| 5,629,594 | A | 5/1997 | Jacobus et al. |
| 5,630,431 | A | 5/1997 | Taylor |
| 5,631,973 | A | 5/1997 | Green |
| 5,636,259 | A | 6/1997 | Khutoryansky et al. |
| 5,649,956 | A | 7/1997 | Jensen et al. |
| 5,657,429 | A | 8/1997 | Wang et al. |
| 5,658,250 | A | 8/1997 | Blomquist et al. |
| 5,667,354 | A | 9/1997 | Nakazawa |
| 5,676,673 | A | 10/1997 | Ferre et al. |
| 5,693,071 | A | 12/1997 | Gorecki et al. |
| 5,695,500 | A | 12/1997 | Taylor et al. |
| 5,695,521 | A | 12/1997 | Anderhub |
| 5,696,574 | A | 12/1997 | Schwaegerle |
| 5,696,837 | A | 12/1997 | Green |
| 5,697,285 | A | 12/1997 | Nappi et al. |
| 5,697,939 | A | 12/1997 | Kubota et al. |
| 5,715,729 | A | 2/1998 | Toyama et al. |
| 5,718,038 | A | 2/1998 | Takiar et al. |
| 5,727,569 | A | 3/1998 | Benetti et al. |
| 5,735,290 | A | 4/1998 | Sterman et al. |
| 5,737,711 | A | 4/1998 | Abe |
| 5,740,699 | A | 4/1998 | Ballantyne et al. |
| 5,749,362 | A | 5/1998 | Funda et al. |
| 5,754,741 | A | 5/1998 | Wang et al. |
| 5,762,458 | A | 6/1998 | Wang et al. |
| 5,765,565 | A | 6/1998 | Adair |
| 5,766,126 | A | 6/1998 | Anderson |
| 5,766,129 | A | 6/1998 | Mochizuki |
| 5,776,126 | A | 7/1998 | Wilk et al. |
| 5,778,889 | A | 7/1998 | Jascomb |
| 5,779,623 | A | 7/1998 | Bonnell |
| 5,784,542 | A | 7/1998 | Ohm et al. |
| 5,785,191 | A | 7/1998 | Feddema et al. |
| 5,792,045 | A | 8/1998 | Adair |
| 5,792,135 | A | 8/1998 | Madhani et al. |
| 5,792,178 | A | 8/1998 | Welch et al. |
| 5,797,900 | A | 8/1998 | Madhani et al. |
| 5,800,423 | A | 9/1998 | Jensen |
| 5,807,284 | A | 9/1998 | Foxlin |
| 5,807,377 | A | 9/1998 | Madhani et al. |
| 5,807,378 | A | 9/1998 | Jensen et al. |
| 5,807,379 | A | 9/1998 | Lesperance, Jr. |
| 5,808,665 | A | 9/1998 | Green |
| 5,810,863 | A | 9/1998 | Wolf et al. |
| 5,810,876 | A | 9/1998 | Kelleher |
| 5,810,879 | A | 9/1998 | De Guillebon |
| 5,810,880 | A | 9/1998 | Jensen et al. |
| 5,813,813 | A | 9/1998 | Daum et al. |
| 5,814,038 | A | 9/1998 | Jensen et al. |
| 5,815,640 | A | 9/1998 | Wang et al. |
| 5,817,084 | A | 10/1998 | Jensen |
| 5,819,206 | A | 10/1998 | Horton et al. |
| 5,825,862 | A | 10/1998 | Voit et al. |
| 5,825,982 | A | 10/1998 | Wright et al. |
| 5,828,813 | A | 10/1998 | Ohm |
| 5,836,869 | A | 11/1998 | Kudo et al. |
| 5,841,950 | A | 11/1998 | Wang et al. |
| 5,844,824 | A | 12/1998 | Newman et al. |
| 5,855,553 | A | 1/1999 | Tajima et al. |
| 5,855,583 | A | 1/1999 | Wang et al. |
| 5,859,934 | A | 1/1999 | Green |
| 5,860,420 | A | 1/1999 | Wiedner et al. |
| 5,860,995 | A * | 1/1999 | Berkelaar ................ 606/174 |
| 5,867,210 | A | 2/1999 | Rod |
| 5,876,325 | A | 3/1999 | Mizuno et al. |
| 5,878,193 | A | 3/1999 | Wang et al. |
| 5,882,206 | A | 3/1999 | Gillio |
| 5,885,583 | A | 3/1999 | Miyazaki et al. |
| 5,887,121 | A | 3/1999 | Funda et al. |
| 5,898,599 | A | 4/1999 | Massie et al. |
| 5,904,702 | A | 5/1999 | Ek et al. |
| 5,906,630 | A | 5/1999 | Anderhub et al. |
| 5,907,664 | A | 5/1999 | Wang et al. |
| 5,931,832 | A | 8/1999 | Jensen |
| 5,938,678 | A | 8/1999 | Zirps et al. |
| 5,950,629 | A | 9/1999 | Taylor et al. |
| 5,950,929 | A | 9/1999 | Collier et al. |
| 5,951,475 | A | 9/1999 | Gueziec et al. |
| 5,951,587 | A | 9/1999 | Qureshi et al. |
| 5,954,692 | A | 9/1999 | Smith et al. |
| 5,954,731 | A | 9/1999 | Yoon |
| 5,957,831 | A | 9/1999 | Adair |
| 5,971,976 | A | 10/1999 | Wang et al. |
| 5,980,782 | A | 11/1999 | Hershkowitz et al. |
| 5,984,932 | A | 11/1999 | Yoon |
| 6,001,108 | A | 12/1999 | Wang et al. |
| 6,007,550 | A | 12/1999 | Wang et al. |
| 6,009,346 | A | 12/1999 | Ostrow |
| 6,024,695 | A | 2/2000 | Taylor et al. |
| 6,063,095 | A | 5/2000 | Wang et al. |
| 6,080,181 | A | 6/2000 | Jensen et al. |
| 6,102,850 | A | 8/2000 | Wang et al. |
| 6,106,511 | A | 8/2000 | Jensen |
| 6,120,433 | A | 9/2000 | Mizuno et al. |
| 6,132,368 | A | 10/2000 | Cooper |
| 6,132,441 | A | 10/2000 | Grace |
| 6,184,868 | B1 | 2/2001 | Shahoian et al. |
| 6,196,081 | B1 | 3/2001 | Yau |
| 6,201,984 | B1 | 3/2001 | Funda et al. |
| 6,213,124 | B1 | 4/2001 | Butterworth |
| 6,223,100 | B1 | 4/2001 | Green |
| 6,226,566 | B1 | 5/2001 | Funda et al. |
| 6,231,526 | B1 | 5/2001 | Taylor et al. |
| 6,236,875 | B1 | 5/2001 | Bucholz et al. |
| 6,244,809 | B1 | 6/2001 | Wang et al. |
| 6,246,898 | B1 | 6/2001 | Vesely et al. |
| 6,259,806 | B1 | 7/2001 | Green |
| 6,270,453 | B1 | 8/2001 | Sakai |
| 6,278,975 | B1 | 8/2001 | Brant et al. |
| 6,296,635 | B1 | 10/2001 | Smith et al. |
| 6,307,285 | B1 | 10/2001 | Delson et al. |
| 6,312,435 | B1 | 11/2001 | Wallace et al. |
| 6,330,837 | B1 | 12/2001 | Charles et al. |
| 6,368,269 | B1 | 4/2002 | Lane |
| 6,368,428 | B1 | 4/2002 | Thiel et al. |
| 6,434,416 | B1 | 8/2002 | Mizoguchi et al. |

(56) References Cited

U.S. PATENT DOCUMENTS

| | | | |
|---|---|---|---|
| 6,436,107 B1 | 8/2002 | Wang et al. |
| 6,468,265 B1 | 10/2002 | Evans et al. |
| 6,490,467 B1 | 12/2002 | Bucholz et al. |
| 6,490,475 B1 | 12/2002 | Seeley et al. |
| 6,574,355 B2 | 6/2003 | Green |
| 6,589,164 B1 | 7/2003 | Flaherty |
| 6,671,581 B2 | 12/2003 | Niemeyer et al. |
| 6,699,177 B1 | 3/2004 | Wang et al. |
| 6,699,235 B2 | 3/2004 | Wallace et al. |
| 6,714,841 B1 | 3/2004 | Wright et al. |
| 6,772,053 B2 | 8/2004 | Niemeyer |
| 6,793,653 B2 | 9/2004 | Sanchez et al. |
| 6,793,669 B2 | 9/2004 | Nakamura et al. |
| 6,804,581 B2 | 10/2004 | Wang et al. |
| 6,817,972 B2 | 11/2004 | Snow |
| 6,852,107 B2 | 2/2005 | Wang et al. |
| 6,871,117 B2 | 3/2005 | Wang et al. |
| 6,905,460 B2 | 6/2005 | Wang et al. |
| 6,905,491 B1 | 6/2005 | Wang et al. |
| 6,949,106 B2 | 9/2005 | Brock et al. |
| 6,951,535 B2 | 10/2005 | Ghodoussi et al. |
| 6,994,703 B2 | 2/2006 | Wang et al. |
| 7,025,064 B2 | 4/2006 | Wang et al. |
| 7,025,761 B2 | 4/2006 | Wang et al. |
| 7,027,892 B2 | 4/2006 | Wang et al. |
| 7,074,179 B2 | 7/2006 | Wang et al. |
| 7,083,571 B2 | 8/2006 | Wang et al. |
| 7,118,582 B1 | 10/2006 | Wang et al. |
| 7,390,325 B2 | 6/2008 | Wang et al. |
| 7,507,199 B2 | 3/2009 | Wang et al. |
| 7,695,481 B2 | 4/2010 | Wang et al. |
| 7,785,320 B2 | 8/2010 | Wang et al. |
| 7,914,521 B2 | 3/2011 | Wang et al. |
| RE43,049 E | 12/2011 | Grace |
| 8,241,306 B2 | 8/2012 | Grace |
| 8,292,916 B2 | 10/2012 | Grace |
| 8,845,681 B2 * | 9/2014 | Grace | 606/205 |
| 2002/0140665 A1 | 10/2002 | Gordon |
| 2003/0065311 A1 | 4/2003 | Wang et al. |
| 2003/0078474 A1 | 4/2003 | Wang et al. |
| 2003/0083648 A1 | 5/2003 | Wang et al. |
| 2003/0083650 A1 | 5/2003 | Wang et al. |
| 2004/0236352 A1 | 11/2004 | Wang |
| 2005/0228365 A1 | 10/2005 | Wang et al. |
| 2005/0234433 A1 | 10/2005 | Wang et al. |
| 2008/0228196 A1 | 9/2008 | Wang et al. |
| 2008/0312668 A1 | 12/2008 | Grace |
| 2011/0087238 A1 | 4/2011 | Wang et al. |
| 2011/0112571 A1 | 5/2011 | Grace |

FOREIGN PATENT DOCUMENTS

| | | |
|---|---|---|
| DE | 9409979 U1 | 9/1994 |
| DE | 4310842 C2 | 1/1996 |
| DE | 4213426 | 1/1997 |
| DE | 29803734 U1 | 4/1998 |
| EP | 239409 | 9/1987 |
| EP | 424687 | 5/1991 |
| EP | 0494343 A2 | 7/1992 |
| EP | 494943 | 8/1995 |
| EP | 0776738 A2 | 6/1997 |
| EP | 0776738 B1 | 4/2002 |
| JP | 6113997 | 4/1994 |
| WO | WO-9104711 | 4/1991 |
| WO | WO-9220295 A1 | 11/1992 |
| WO | WO-9313916 A1 | 7/1993 |
| WO | WO-9403113 A1 | 2/1994 |
| WO | WO-9418881 A1 | 9/1994 |
| WO | WO-9426167 | 11/1994 |
| WO | WO-9426167 A1 | 11/1994 |
| WO | WO-9501757 | 1/1995 |
| WO | WO-9516396 A1 | 6/1995 |
| WO | WO-9530964 A1 | 11/1995 |
| WO | WO-9715240 A1 | 5/1997 |
| WO | WO-9822030 A1 | 5/1998 |
| WO | WO-9825666 A1 | 6/1998 |
| WO | WO-9834543 A1 | 8/1998 |
| WO | WO-9858589 A1 | 12/1998 |

OTHER PUBLICATIONS

Abstract of a presentation "A Pneumatic Controlled Sewing Device for Endoscopic Application the MIS Sewing Instrument MSI" given at the 3rd World Congress of Endoscopic Surgery in Bordeaux, Jun. 18-20, 1992, 1 page.

Abstract of a presentation given at the 3rd World Congress of Endoscopic Surgery in Bordeaux entitled "Session 15/1", Jun. 18-20, 1992, 1 page.

Abstract of a presentation given at the 3rd World Congress of Endoscopic Surgery in Bordeaux, entitled "Session 15/2", Jun. 18-20, 1992, 1 page total.

Abstract of a presentation given at the 3rd World Congress of Endoscopic Surgery in Bordeaux entitled "Session 15/4", Jun. 18-20, 1992, 1 page.

Abstract of a presentation given at the 3rd World Congress of Endoscopic Surgery in Bordeaux entitled "Session 15/5", Jun. 18-20, 1992, 1 page.

Adams, Ludwig et al., "Computer-Assisted Surgery," IEEE Computer Graphics & Applications, May 1990, pp. 43-52, vol. 10—Issue 3, IEEE Computer Society Press.

Adhami, Louai et al., "Planning and simulation of robotically assisted minimal invasive surgery," Proceedings of the Third International Conference on Medical Image Computing and Computer-Assisted Intervention, 2000, 11 pages, vol. 1935, Springer-Verlag.

Alexander, Arthur D., "A Survey Study of Teleoperators Robotics and Remote Systems Technology," Remotely Manned Systems Exploration and Operation in Space, California Institute of Technology, 1973, pp. 449-458.

Alexander, Arthur D. III, "Impacts of Telemation on Modern Society," Symposium on Theory and Practice of Robots and Manipulators, Centre for Mechanical Sciences 1st CISM IFToMM Symposium, Sep. 5-8, 1974, pp. 121-136, vol. 2, Springer-Verlag.

Arai H., et al., "Position Control System of a Two Degree of Freedom Manipulator with a Passive Joint," IEEE Transactions on Industrial Electronics, 1991, vol. 38 (1), pp. 15-20.

Bauer, W. et al., "Virtual reality as interface for interaction and manipulation in endoscopy," Minimally Invasive Therapy, 1995, pp. 319-339, vol. 4, Blackwell Science Ltd.

Bejczy, Antal K. et al., "Controlling Remote Manipulators through Kinesthetic Coupling," Computers in Mechanical Engineering, 1983, pp. 48-60, vol. 1-Issue 1.

Ben Gayed, M. et al., "An Advanced Control Micromanipulator for Surgical Application," Systems Science, 1987, pp. 23-34, vol. 13 No. 1-2ol 13 No. 1-2.

Ben Gayed, M. et al., "An Advanced Control Micromanipulator for Surgical Applications," Systems Science, 1987, pp. 123-134, vol. 13.

Besant, Colin et al., Abstract of presentation "Camera Control for Laparoscopic Surgery by Speech recognizing Robot: Constant Attention and Better Use of Personnel," 3rd World Congress of Endoscopic surgery, 1992, p. 271, vol. 3-issue 3.

Brief Communication, mailed Jun. 2002, for EP Patent No. EP 0653922 B, including Affidavit by Alberic George T.W. Fiennes signed May 20, 2002 relating to Besant Abstract and NASA presentation by Keith L. Doty, "Kinematic Analysis of the Arid Manipulator" given on Aug. 7, 1992 at the Univ. of Florida, Gainesville, FL (52 pp.).

Charles, Steve et al., "Design of a Surgeon Machine Interface for Teleoperated Microsurgery," Proceedings of IEEE Annual Conference on Engineering in Medicine and Biology, 1989, pp. 0883-0884, vol. 11, IEEE.

Colgate, Edward, J., "Power and Impedance Scaling in Bilateral Manipulation," IEEE International Conference on Robotics and Automation, Sacramento, California, Apr. 1991, pp. 2292-2297, vol. 3, IEEE.

Corcoran, Elizabeth, "Robots for the Operating Room," The New York Times, 2 pages total, Jul. 19, 1992, Section 3 Page 9C.

(56) References Cited

OTHER PUBLICATIONS

Das, Hari et al., "Kinematic Control and Visual Display of Redundant Teleoperators," IEEE International Conference on Systems, Man, and Cybernetics, 1989, pp. 1072-1077, vol. 3, IEEE.
Davies, Brian L. et al., "A Surgeon Robot for Prostatectomies," Fifth International conference on Advanced Robotics, 1991, pp. 871-875, vol. 1, IEEE.
Declaration by J. Kenneth Salisbury, Jr., In Support of Prosecution of U.S. Appl. No. 08/709,930, filed May 11, 2000, (pp. 1-10); Appendix A: Massachusetts Institute of Technology, School of Engineering Faculty Personnel Record for J. Kenneth Salisbury, Jr., pp. 1-25; Appendix B: Ogata, Katsuhiko, Modern Control Engineering, Chapter 1 "Introduction to Control Systems Analysis" pp. 1-4, 8-9, (1990) Second Edition, Prentice Hall, Englewood Cliffs, New Jersey; Appendix C: Franklin, Gene, F. et al., Feedback Control of Dynamic Systems, Chapter 1, "An Overview and Brief History of Feedback Control" pp. 1, 3-4, 9-10, (1994) Third Edition, Addison-Wesley Publishing Company, Reading, Massachusetts.
Dolan, J.M. et al., "A Robot in an Operating Room: A Bull in a China Shop," 1987, pp. 1096-1097, vol. 2.
EP Patent Application No. 00921806.6 Extended European Search Report, mailed on Jul. 9, 2004, 3 pages.
EP Patent Application No. 08017470.9 Extended European Search Report, mailed Oct. 28, 2009, 6 pages.
European Search Report for Application No. EP09173820 mailed on Feb. 15, 2012, 4 Pages.
Finlay, Patrick A. et al., "Controlling the movement of a surgical laparoscope," Engineering in Medicine and Biology Magazine, May/Jun. 1995, pp. 289 291, vol. 14-Issue 3, IEEE.
Fu, K.S. et al., "Robotics: control, sensing, vision, and intelligence," 1987, pp. 12-76 and 201-265, Ch. 2 & 5, McGraw-Hill Company.
Green, Philip S., "A Pneumatic Controlled Sewing Device for Endoscopic Application the MIS Sewing Instrument MSI," Abstract No. 7, 1992.
Green, Philip S. et al., Abstract of a presentation, "Telepresence: Advanced Teleoperator Technology for Minimally Invasive Surgery," 1992 Medicine Meets Virtual Reality (MMVR) symposium in San Diego, Jun. 4-7, 1992, 1 page.
Green, Philip S. et al., Abstract of a presentation "Telepresence: Advanced Teleoperator Technology for Minimally Invasive Surgery," given at the 3rd World Congress of Endoscopic Surgery in Bordeaux, Jun. 18-20, 1992, 2 pages total, abstract 704.
Green, Philip S. et al., Statutory Declaration by Dr. Phillip S. Green, the presenter of the video entitled "Telepresence Surgery: The Future of Minimally Invasive Medicine," European Patent Convention in the Matter of EP-B-653922. 32 pages, Sep. 12, 2000.
Green P.S., et al., "Telepresence Surgery," IEEE Engineering in Medicine and Biology Magazine, IEEE Service Center, Pisacataway, NJ, US, May 1, 1995, vol. 14 (3), pp. 324-329, XP000505090.
Guerrouad, Aicha et al., "SMOS: Stereotaxical Microtelemanipulator for Ocular Surgery," IEEE Engineering in Medicine & Biology Society 11th international conference, Nov. 9-12, 1989, pp. 879-880, vol. 3, IEEE.
Hill, John W., "Telepresence surgery demonstration system," Robotics and Automation, 1994, pp. 2302-2307, vol. 3, SRI International.
Hurteau et al., "Laparoscopic surgery assisted by a robotic cameraman: Concept and Experimental results," IEEE International Conference on Robotics and Automation, May 8-13, 1994, pp. 2286-2289, vol. 3, IEEE.
Inoue, Masao; "Six-Axis bilateral control of an articulated slave manipulator using a Cartesian master manipulator," Advanced robotics, 1990, pp. 139-150, vol. 4-Issue 2, Robotic society of Japan.
International Search Report for application No. PCT/US93/07343, Mailed on Dec. 16, 1993, 1 page.
International Search Report for application No. PCT/US94/09442, Mailed on Jan. 9, 1995, 2 pages.
International Search Report for application No. PCT/US97/02628, Mailed on Jul. 3, 1997, 1 page.
International Search Report for application No. PCT/US99/27632, Mailed on Feb. 23, 2001, 2 pages.
Jackson, Bernie G. et al., "Force Feedback and Medical Simulation," Interactive Technology and the New Paradigm for Healthcare, Morgan et al. (Eds ), 1995, pp. 147-151, vol. 24, IOS Press and Ohms.
Jau, B. M., "Anthropomorphic Remote Manipulator," NASA Tech Briefs, Apr. 1991, p. 82, NASA's Jet Propulsion Laboratory, Pasadena, California.
Kavoussi, Louis R. et al., "Telerobotic Assisted Laparoscopic Surgery: Initial Laboratory and Clinical Experience," Urology, Jul. 1994, pp. 15-19, vol. 44—Issue 1.
Kazerooni, H., "Human/Robot Interaction via the Transfer of Power and Information Signals Part I: Dynamics and Control Analysis," IEEE International Conference on Robotics and Automation, 1989, pp. 1632-1640, IEEE.
Kazerooni, H, "Human/Robot Interaction via the Transfer of Power and Information Signals—Part II," An Experimental Analysis, Proc. of the 1989 IEEE International Conference on Robotics and Automation, 1989, pp. 1641-1647, vol. 3, IEEE.
Krishnan, S.M. et al., Abstract of a presentation "Design Considerations of a New Generation Endoscope Using Robotics and Computer Vision Technology," given at the 3rd World Congress of Endoscopic Surgery in Bordeaux, Jun. 18-20, 1992, 1 page.
Lavallee, Stephane, "A New System for Computer Assisted Neurosurgery," IEEE Eng. in Med. & Biol. Soc. 11th Annual International Conference, Jun. 1989, pp. 926-927, vol. 11.
Lavallee, Stephane et al., "Image guided operating robot: a clinical application in stereotactic neurosurgery," Proceedings of the 1992 IEEE International Conference on Robotics and Automation, 1992, pp. 618-624, IEEE.
Mair, Gordon M., Industrial Robotics, Prentice Hall, 1988, pp. 41-43, 49-50, 54, 203-209.
Majima S. et al., "On a Micro Manipulator for Medical Application Stability Consideration of its Bilateral Controller Mechatronics," 1991, pp. 293-309, vol. 1—Issue 3.
Melzer, Abstract of a presentation "Concept and Experimental Application of a Surgical Robotic System the Steerable MIS Instrument SMI," given at the 3rd World Congress of Endoscopic Surgery in Bordeaux, Jun. 18-20, 1992, 1 page total.
Minutes of the Oral Proceedings before the Opposition Division for EP Application No. 93 919 884.2 (Patent No. EP 0653922 B) between *Computer Motion, Inc.* v. *Intuitive Surgical, Inc.*, Jul. 24, 2002.
Neisius B. et al., "Robotic manipulator for endoscopic handling of surgical effectors and cameras," 1st Intl. Symposium on Medical Robotics and Computer Assisted Surgery, 1994, pp. 169-176, vol. 2.
Notice of Opposition European Patent Office dated, Sep. 14, 2000, pp. 1-27.
Patent Interference, "USPTO Patent Interference No. 104644, Wang et al. vs. P. Green," May 28, 2002, 135 pages total. cited by other.
PCT/US00/09201 International Search Report, mailed Aug. 30, 2000, 1 page.
Preising, B. et al. "A Literature Review: Robots in Medicine," IEEE Engineering in Medicine and Biology, 1991, pp. 13-22, 71, vol. 10—Issue 2, IEEE.
Rasor, Ned S. et al., "Endocorporeal Surgery Using Remote Manipulators," Proceedings of the First National Conference held at California Institute of Technology, 1972, pp. 483-492.
Riviere, Cameron N. et al., "Adaptive Real Time Canceling of Physiological Tremor for Microsurgery," Proceedings of the Second International Symposium on Medical Robotics and Computer Assisted Surgery, 1995, pp. 89-96.
Sabatini, A. M. et al., "Force Feedback Based Telemicromanipulation for Robot Surgery on Soft Tissue," IEEE Engineering in Medicine and Biology Society 11th Annual International Conference, 1989, pp. 890-891, vol. 3, IEEE.
Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.
Schurr, M.O et al., "Experimental Telemanipulation in Endoscopic Surgery," Surgical Laparoscopy & Endoscopy, 1996, pp. 167-175, vol. 6—Issue 3.
Sukthankar, Sujat M. et al., "Force Feedback Issues in Minimally Invasive Surgery," Interactive Technology and the New Paradigm for Healthcare, 1995, pp. 375-379, vol. 56, IOS Press and Ohmsha.

(56) References Cited

OTHER PUBLICATIONS

Summons to Attend Oral Proceedings Pursuant to Rule EPC mailed 13 for Patent No. EP 0653922 B, Mar. 2002, (28 pgs total), vol. 71—Issue 1.

Supplementary European Search Report for Application No. EP00914788, mailed on Mar. 11, 2009, 5 pages.

Supplementary European Search Report for Application No. EP93919884 mailed on Apr. 5, 1995, 4 Pages.

Supplementary Partial European Search Report for Application No. EP97906691, mailed on Jul. 11, 2000, 4 pages.

Taubes, Gary et al., "Surgery in Cyberspace," Discover magazine, Dec. 1994, vol. 15, issue 12, pp. 85-92.

Taylor, Russell H. et al., "A Telerobotic Assistant for Laparoscopic Surgery," IEEE Engineering in Medicine and Biology, May/Jun. 1995, pp. 279-288, vol. 14, Issue 3, IEEE.

Taylor, Russell H. et al., "Research Report: A Telerobotic Assistant for Laparoscopic Surgery," Accepted to IEEE EIMBS Magazine, Special Issue on "Robotics in Surgery," Dec. 1994, 24 pages.

Taylor, Russell H. et al., "Robotic Total Hip Replacement Surgery in Dogs," Proceedings of the Annual International Conference of the IEEE Engineering in Medicine and Biology Society, 1989, pp. 887-889, vol. 9—Issue 12, IEEE.

Taylor, Russell H. et al., "Taming the Bull: Safety in a Precise Surgical Robot," Fifth International Conference on Advanced Robotics (91 ICAR), Jun. 19-22, 1991, vol. 1, pp. 865-870, IEEE.

Tejima, Noriyuki et al., "A New Microsurgical Robot System for Corneal Transplantation," Precision Machinery, 1988, pp. 1-9, vol. 2, Gordon and Breach Science Publishers Inc.

Tendick Frank, et al., "Analysis of the Surgeon's Grasp for Telerobotic Surgical Manipulation," IEEE 11th Annual Int Conf on Engineering in Medicine and Biology, Jun. 1989, pp. 914-915, IEEE.

Thring, M.W., Robots and Telechirs: Manipulators with Memory; Remote Manipulators; Machine Limbs for the Handicapped, 1983, pp. 9-11, 108-131, 194-195, 235-279; Ellis Horwood Limited, Chapter 5,7,8,9.

Transcript of a video presented by SRI at the 3rd World Congress of Endoscopic Surgery in Bordeaux, France on Jun. 18-20, 1992; in Washington D.C. on Apr. 9, 1992; and San Diego, CA on Jun. 4-7, 1992; entitled "Telepresence Surgery: The Future of Minimally Invasive Medicine," 3 pages.

Trevelyan, James P. et al., "Motion Control for a Sheep Shearing Robot," IEEE Robotics Research Conference, the 1st International Symposium, Carroll, NH, USA., 1983, pp. 175-190, in Robotics Research, MIT Press.

Vertut, Jean and Phillipe Coiffet, Robot Technology: Teleoperation and Robotics Evolution and Development, English translation, Prentice-Hall, Inc. Inglewood Cliffs, NJ, USA 1986, vol. 3A, 332 pages.

Vibet, C., "Properties of Master Slave Robots," Motor-con, 1987, pp. 309-316.

Video presented by SRI at the 3rd World Congress of Endoscopic Surgery in Bordeaux on in Washington on Apr. 9, 1992 and in San Diego CA on entitled Telepresence Surgery The Future of Minimally Invasive Medicine (VHS Tape), Jun. 4-7, 1992 Jun.

Wapler, M., "Medical manipulators—A Realistic Concept", Minimally Invasive Therapy, 1995, pp. 261-266, vol. 4, Blackwell Science Ltd.

Wolf, Stanley et al., Student Reference Manual for Electronic Instrumentation Laboratories, 1990, pp. 498 and 499, Prentice Hall New Jersey.

\* cited by examiner

RIGIDLY-LINKED ARTICULATING WRIST WITH DECOUPLED MOTION TRANSMISSION

CROSS-REFERENCE TO RELATED APPLICATIONS

This application is a continuation of U.S. patent application Ser. No. 13/633,963, filed Oct. 3, 2012, now U.S. Pat. No. 8,845,681, which is a continuation of U.S. patent application Ser. No. 11/948,052, filed Nov. 30, 2007, now U.S. Pat. No. 8,292,916, which is a division of U.S. patent application Ser. No. 10/013,170, filed Jun. 7, 2002, now U.S. Pat. No. RE43049, which is a continuation-in-part of application Ser. No. 09/262,134, filed Mar. 3, 1999, now U.S. Pat. No. 6,436,107, which is a continuation-in-part of application Ser. No. 08/873,190, filed Jun. 11, 1997, now U.S. Pat. No. 6,102,850, which is a continuation-in-part of application Ser. No. 08/755,063, filed Nov. 22, 1996, now U.S. Pat. No. 5,855,583.

BACKGROUND OF THE INVENTION

1. Field of the Invention

The present invention generally relates to surgical devices. More particularly, the present invention relates to a device for suturing during the performance of minimally invasive endoscopic surgical procedures and more particularly to an articulating device for use in endoscopic coronary artery by-pass grafting surgery.

2. Description of Related Art

Blockage of a coronary artery may deprive the heart of the blood and oxygen required to sustain life. The blockage may be removed with medication or by an angioplasty. For severe blockage, a coronary artery bypass graft (CABG) is performed to bypass the blocked area of the artery. CABG procedures are typically performed by splitting the sternum and pulling open the chest cavity to provide access to the heart. An incision may be made in the artery adjacent to the blocked area. The internal mammary artery (IMA) or some other arterial source of blood-flow may then be severed and attached to the artery at the point of incision. The IMA bypasses the blocked area of the artery to again provide a full flow of blood to the heart.

Splitting the sternum and opening the chest cavity can create tremendous trauma on the patient. Additionally, the cracked sternum prolongs the recovery period of the patient. As such, there have been developed systems that enable minimally invasive CABG procedures. These systems utilize hand held tools and small incisions, on the order of 3-5 inches in length, to provide access to the thoracic region of a patient.

Such minimally invasive procedures are conducted by inserting surgical instruments through small incisions, on the order of inches in the skin of the patient. Manipulating such instruments can be awkward, particularly when suturing a graft to an artery. These systems utilize direct visualization of the surgical site. Such systems do not enable a completely endoscopic approach to the CABG procedure because of the need for direct visualization of the site. Additionally, such systems do not enable a fully endoscopic approach because of the incision size necessary to adequately manipulate the surgical instruments at the surgical site.

A fully endoscopic approach utilizes small holes to provide access to the thoracic cavity. Each of these holes is on the order of 3-11 mm in diameter. In order to perform a CABG procedure in a fully endoscopic fashion (i.e. using 3-11 mm holes) a robotic system must be used to filter hand tremors and scale motions made by the surgeon.

To facilitate the performance of an endoscopic surgical procedure, it would be useful to employ surgical instruments that can maneuver to the surgical site as well as manipulate tissue or sutures to perform an anastomosis.

To help minimize risk to the patient, and to minimize operating time, what is needed in the art is a robotically actuated surgical device that can articulate as well as actuate without being overly complex in design.

SUMMARY OF THE INVENTION

The present invention is an articulating device for tissue and needle manipulation, the device comprising:

An elongated housing having a proximal end and a distal end;

an articulation rod extending interior the housing, the articulation rod having a proximal end and a distal end;

an actuation rod extending interior the housing, the actuation rod having a proximal end and a distal end;

a rack driver in communication with the actuation rod at the distal end thereof, the rack driver engaged with a cylindrical rack for translating the motion of the actuation rod substantially about ninety degrees; and a jaw in communication with the cylindrical rack, whereby movement of the cylindrical rack actuates the jaw, the jaw further in pivotal communication with the articulation rod such that linear movement of the articulation rod produces rotational movement of the jaw.

DETAILED DESCRIPTION OF THE INVENTION

Figure 1:
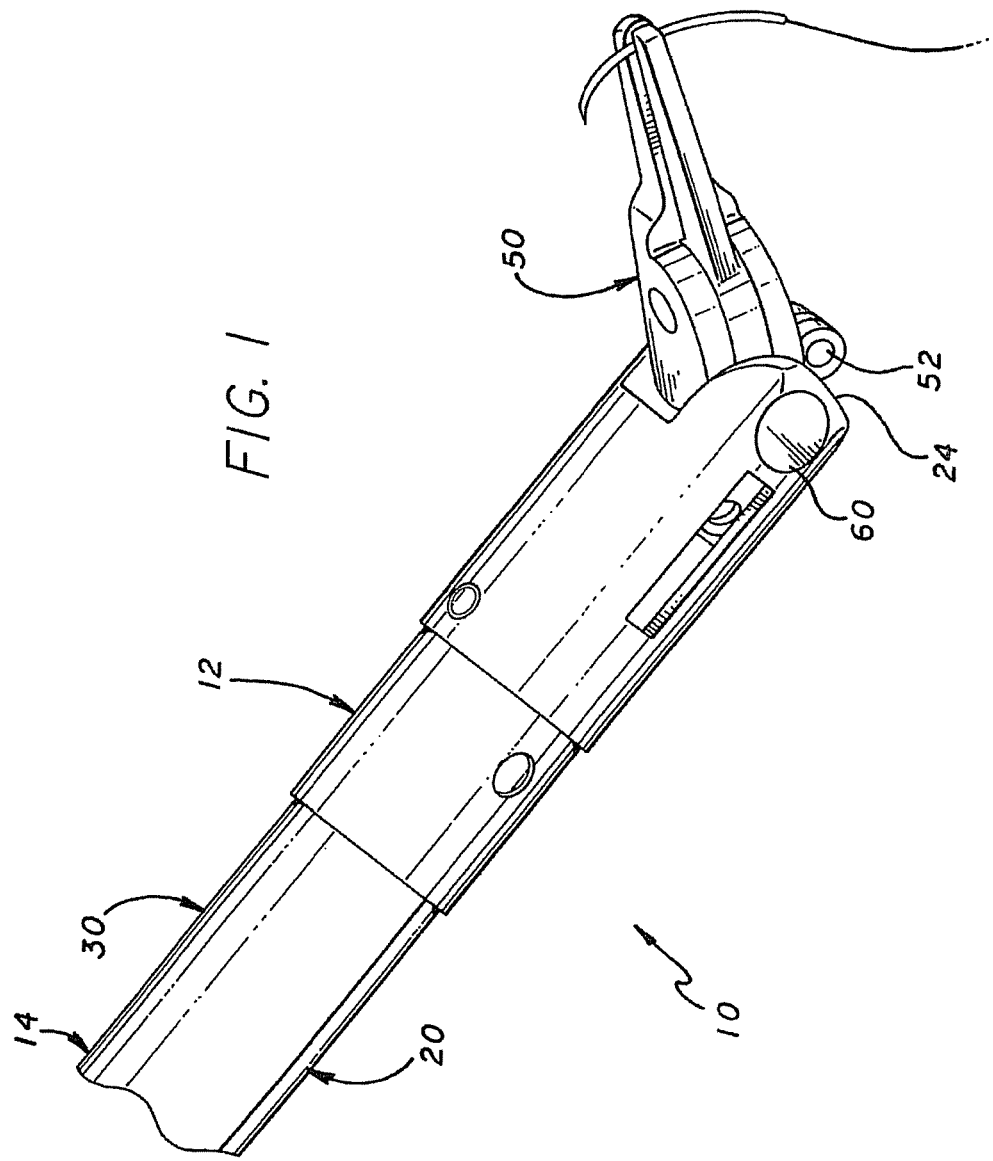
FIG. 1 is a partial break-away perspective view of a device in accordance with the present invention in a closed angled configuration.
Figure 2:
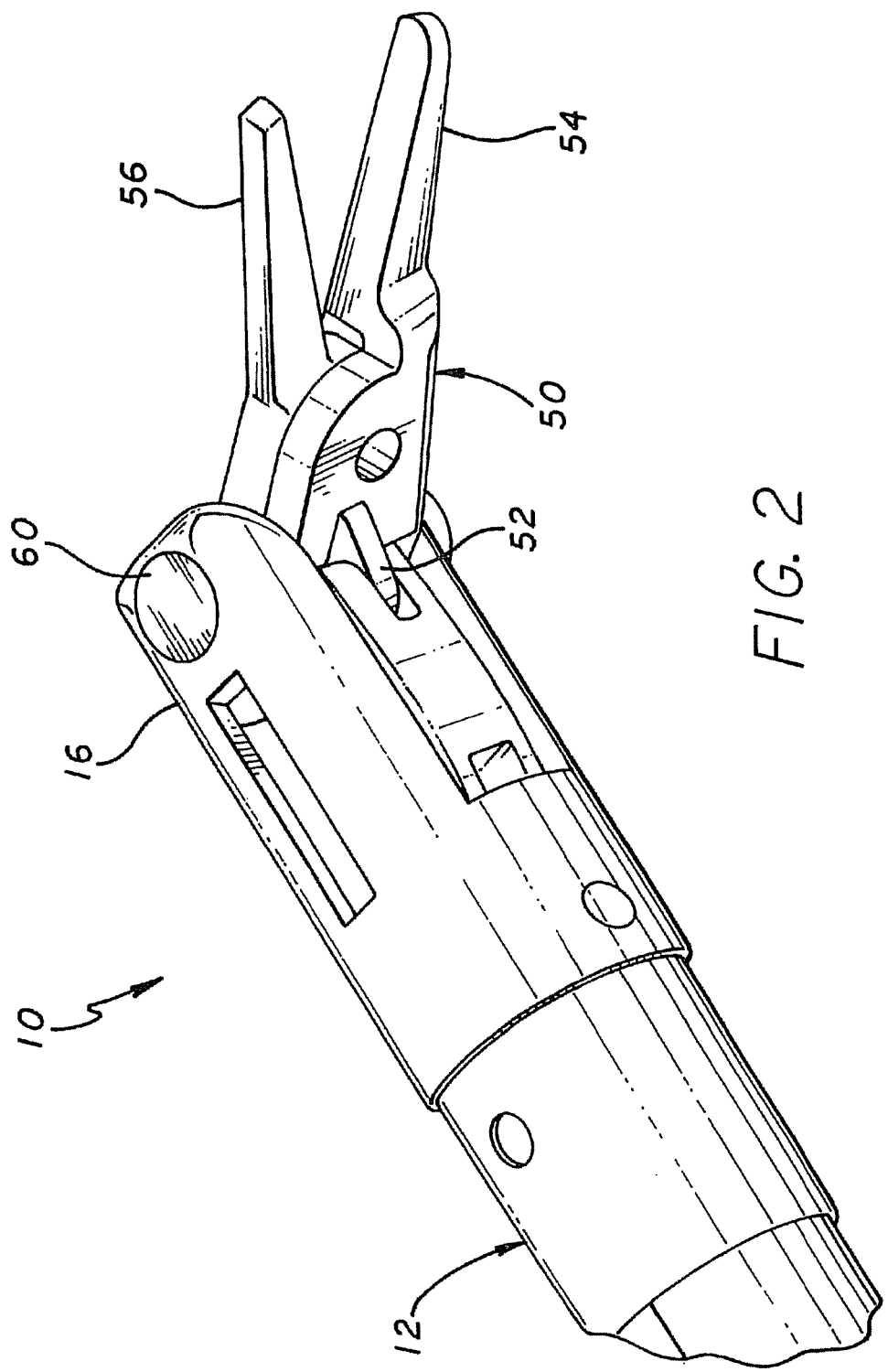
FIG. 2 is a partial break-away perspective view of a device in accordance with the present invention in an open angled configuration.
Figure 3:
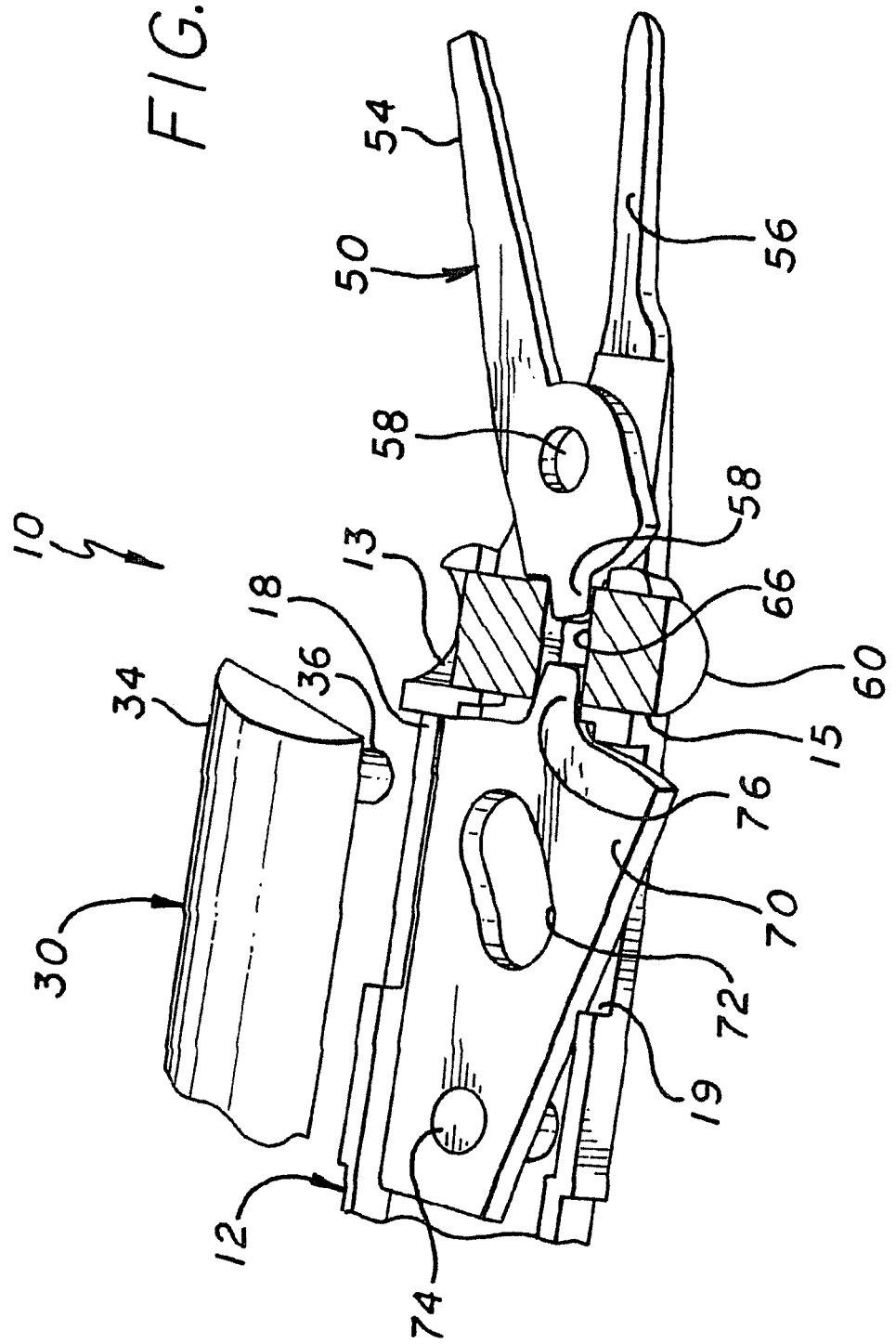
FIG. 3 is a cross-sectional perspective view of a device in accordance with the present invention in an opened straight configuration.

Referring to the drawings more particularly by reference numbers, FIGS. 1, 2 and 3 show a preferred embodiment of the articulating actuating device 10. The device 10 includes a housing 12. The housing extends substantially the length of the instrument 10 and has a proximal end 14 and a distal end 16 and a longitudinal axis X. Disposed interiorly the housing 12 is an articulation rod 20 and an actuation rod 30. Each of the articulation rod 20 and the actuation rod 30 have respective proximal ends 22, 32 and distal ends 24, 34.

The proximal ends 22, 32 of the rods may be attached to a robotic system for the performance of minimally invasive surgical procedures. One such system is produced by Computer Motion, Inc. The assignee hereof and is described in U.S. Pat. No. 5,855,583, which is incorporated herein by reference.

The rods 20, 30 are attached to actuators via attachment means taught in U.S. Pat. No. 5,855,583. Other means for removably attaching a rod to an actuator are known in the art including the use of screws, clips or the like. In this way, each of the rods 20, 30 may be driven by the actuator which is connected to various user interfaces and power sources and are conducive to the performance of minimally invasive surgical procedures.

The articulation rod 20 extends substantially the length of the housing 12 along its longitudinal axis X. The articulation rod 20 is pivotally connected to a jaw 50. Such a pivotal connection may be accomplished through the use of a hinge 52 attached intermediate the articulation rod 20 and the jaw 50.

The jaw 50 pivotally communicates with the housing 12 at the distal end 16 thereof through the use of a rack 60. In this way, motion of the articulation rod 20 results in rotation of the jaw 50. The rack 60 provides a pivot about which the jaw 50 rotates.

The actuation rod 30 provides for actuation of the jaw 50. The actuation rod has a pin 36 disposed at the distal end 34 thereof. The pin 36 seats in a rack channel 72 disposed in a rack driver 70. The rack driver is pivotally attached to the housing 12 via a pin 74 or the like. The housing has two longitudinal apertures 18, 19 formed therethrough at the distal end 16 thereof to provide for lateral movement of the rack driver 70 which shall be described in detail hereinbelow.

Longitudinal motion of the actuation rod 30 moves the pin 36 in the rack channel 72 which translates the longitudinal motion of the actuation rod 30 into a pivotal motion of the rack driver 70. The rack driver 70 pivots about the pivot point defined by the pin 74 which attaches the rack driver 70 to the housing 12. The rack driver 70 may move outside of the space defined as the interior of the housing through the longitudinal apertures 18, 19.

The rack driver 70 has a shoulder 76 which engages the rack 60. As the rack driver 70 pivots, the shoulder 76 causes the rack 60 to move laterally, which is orthogonal to the longitudinal motion of the actuation rod 30 and orthogonal to the longitudinal axis of the housing 12. The rack 60 is slidably moveable within the housing 12 through two cylindrical apertures 13, 15 formed therethrough. As the rack 60 moves laterally, the jaw 50 is actuated. The lateral movement of the rack 60 is transferred to a first jaw element 54. A second jaw element 56 is pivotally connected to the first jaw element 54 via a pin 58 or the like and is held stationary with respect to the first jaw element 54. In this way, as the first jaw element is 54 is moved, the second jaw element 56 remains stationary and the jaw 50 is actuated. If each element has a sharp edge, then the jaw may function as a scissors.

The jaw 50 is always in communication with the rack 60, even as it is articulated through the motion of the articulation rod 20. This is accomplished through the use of a cylindrical rack having a circumferential channel 66 formed therein. The channel 66 receives the shoulder 76 of the rack driver 70 as well as a shoulder 58 on the first jaw element 54. As such, as the jaw 50 is articulated, the shoulder 58 on the first jaw element 54 rotates within the circumferential channel 66 in the rack 60 maintaining communication therein and providing for actuation of the jaw 50 regardless of the articulated position of the jaw 50 caused through motion of the articulation rod 20.

In this fashion, the articulation of the jaw 50 and the actuation of the jaw 50 are decoupled. It is highly advantageous to provide for a rigidly linked device that is decoupled in this fashion for several reasons. First, the device is easily steralizable and secondly, the device is quite safe to use as there is no use of tensioned cables or the like.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. An apparatus comprising:
    a housing having a longitudinal axis, a proximal end, and a distal end;
    a jaw element pivotally attached to the distal end of the housing;
    an actuation rod extending from the proximal end of the housing to the distal end;
    a rack driver pivotally attached to the housing at a pivot point, movement of the actuation rod causing pivotal movement of the rack driver about a first axis perpendicular to the longitudinal axis;
    a rack coupling movement of the rack driver to pivotal movement of the jaw element, the rack pivotally movable along a second axis skew to the first axis and perpendicular to the longitudinal axis.

2. The apparatus of claim 1, further comprising:
    a rack driver shoulder disposed on the rack driver;
    a jaw element shoulder disposed on the jaw element;
    a channel formed in the rack for receiving the rack driver shoulder and the jaw element shoulder.

3. The apparatus of claim 1, further comprising:
    a rack driver shoulder disposed on the rack; and
    a rack driver channel disposed on the rack driver for receiving the rack driver shoulder.

4. The apparatus of claim 1, further comprising:
    a jaw element shoulder disposed on the rack; and
    a jaw element channel disposed on the jaw element for receiving the jaw element shoulder.

* * * * *